(12) United States Patent
Walkenhorst et al.

(10) Patent No.: US 8,690,928 B1
(45) Date of Patent: Apr. 8, 2014

(54) FUSION PLATE WITH DIRECTIONAL HOLES AND IMPLANT SYSTEM EMPLOYING THE SAME

(71) Applicant: Lanx, Inc., Broomfield, CO (US)

(72) Inventors: Jared Walkenhorst, Denver, CO (US); Ryan Watson, Boulder, CO (US)

(73) Assignee: Lanx, Inc., Broomfield, CO (US)

( * ) Notice: Subject to any disclaimer, the term of this patent is extended or adjusted under 35 U.S.C. 154(b) by 0 days.

(21) Appl. No.: 13/948,846

(22) Filed: Jul. 23, 2013

(51) Int. Cl.
*A61B 17/80* (2006.01)

(52) U.S. Cl.
USPC ......... 606/287; 606/282; 606/293; 923/17.16

(58) Field of Classification Search
USPC ............... 606/280, 282, 287, 293; 623/17.11, 623/17.16
See application file for complete search history.

(56) References Cited

U.S. PATENT DOCUMENTS

| | | | |
|---|---|---|---|
| 2005/0101960 A1* | 5/2005 | Fiere et al. | 606/72 |
| 2006/0122602 A1* | 6/2006 | Konieczynski et al. | 606/69 |
| 2009/0182430 A1* | 7/2009 | Tyber et al. | 623/17.16 |

* cited by examiner

*Primary Examiner* — Andrew Yang
*Assistant Examiner* — Olivia C Chang
(74) *Attorney, Agent, or Firm* — Perkins Coie LLP

(57) ABSTRACT

A fusion plate for use in fusing two bones together can include directional fastener bores that restrict the angle at which the fasteners can be positioned when inserted through the fastener bores. The fusion plate can be used in conjunction with a spacer, which may include a cavity into which the fusion plate can rest. The fusion plate can be coupled to the spacer using a coupling mechanism.

21 Claims, 18 Drawing Sheets

FUSION PLATE WITH DIRECTIONAL HOLES AND IMPLANT SYSTEM EMPLOYING THE SAME

BACKGROUND

The human spine contains a series of bony segments separated by discs and coupled together with muscle, ligaments, and other connective tissues. A large number of ailments may afflict one or more of these components. One exemplary ailment generally occurs with age as the spinal discs begin to break down, or degenerate resulting in the loss of fluid in the discs, and consequently, the discs become less flexible. Likewise, the discs become thinner allowing the vertebrae to move closer together. Degeneration also may result in tears or cracks in the outer layer, or annulus, of the disc. Degeneration of the annulus may allow the disc to begin to bulge outwardly. In more severe cases, the inner material of the disc, or nucleus, may extrude out of the disc. In addition to degenerative changes in the disc, the spine may undergo changes due to trauma from automobile accidents, falls, lifting, and other activities. Furthermore, in a process known as spinal stenosis, the spinal canal narrows due to excessive bone growth, thickening of tissue in the canal (such as ligament), or both. In all of these conditions, the spaces through which the spinal cord and the spinal nerve roots pass may become narrowed leading to pressure on the nerve tissue which can cause pain, numbness, weakness, or even paralysis in various parts of the body. Finally, the facet joints between adjacent vertebrae may degenerate and cause localized and/or radiating pain. All of the above conditions, as well as others not specifically mentioned, are collectively referred to herein as spine disease.

Conventionally, surgeons treat spine disease by attempting to restore the normal spacing between adjacent vertebrae. This may be sufficient to relieve pressure from affected nerve tissue. However, it is often necessary to surgically remove disc material, bone, or other tissues that impinge on the nerve tissue and/or to debride the facet joints. Most often, the restoration of vertebral spacing is accomplished by inserting a rigid spacer made of bone, metal, or plastic into the disc space between the adjacent vertebrae and allowing the vertebrae to grow together, or fuse, into a single piece of bone. The vertebrae are typically stabilized during this fusion process with the use of fusion plates and/or pedicle screws fastened to the adjacent vertebrae. The fusion plates used with the spacers are typically coupled to the spacer with a first fastening means and are positioned on the spacer such that one or more flanges extend beyond the spacer. These flanges can include one or more holes through which pedicle screws are inserted to fasten the fusion plate to the bone.

Although techniques for placing intervertebral spacers, plates, and pedicle screw fixation systems have become less invasive in recent years, they still require the placement of hardware deep within the surgical site adjacent to the spine. Extreme care needs to be taken when placing the hardware deep within the surgical site due to, for example, the close proximity of vessels and nerves to the surgical site. Of specific concern are the screws or other fastening devices used to fasten the fusion plate to the bone. If the screws are not properly aligned when driven into the bone, they may impact the nerves or vessels, which can cause severe injury to the patient. Issues with improper or incomplete placement of the hardware at the disc space can also arise if a screw is driven into the bone in a direction that results in the screw impacting a screw that has already been placed in the bone.

Thus, it would be desirable to provide a fusion plate for use with an implantable intervertebral spacer that will restrict the screw trajectory variability so as to reduce or eliminate the possibility for human error when installing the fusion system.

SUMMARY

In some embodiments, a fusion plate including directional fastener bores is disclosed. The directional fastener bores restrict the angle at which a fastener can be oriented when inserted in the fastener bore. This can help to prevent human error where a fastener is angled in a direction that results in the fastener contacting and/or damaging areas around the bone, such as vessels and nerves. In some embodiments, the fusion plate includes a main body portion and one or more extension side portions extending from the sides of the main body portion. The main body portion can include a forward face and a rearward face opposite the forward face. The extension side portions can include a forward face, a rearward face opposed to the forward face and one or more fastener bores. The fastener bores generally extend from the forward face to the rearward face of the extension side portion. The fastener bore can further include a first opening in the rearward face and a second opening in the forward face. Located intermediate the first opening and the second opening is a throat portion. The first opening has a first diameter extending from a first side of the first opening closest to the main body to an opposing side of the first opening. The second opening has a second diameter extending from a first side of the second opening closest to the main body to an opposing side of the second opening. The throat portion includes a third diameter extending from a first side of the throat portion closest to the main body to an opposing side of the throat portion. In some embodiments, the third diameter is shorter than the first and second diameters. This configuration generally forms a fastener bore having an hourglass shape. Each of the first opening, second opening, and throat portion can include a perpendicular diameter that is perpendicular to the first diameter, second diameter, and third diameter, respectively. The length of diameters perpendicular to the second and third diameters can be generally equal. The above configuration provides for a fastener to be angled in a direction parallel with the longitudinal axis of the fusion plate, but restricts angling the fastener in a direction perpendicular to the longitudinal axis of the fusion plate.

In some embodiments, an implant configured to be interposed between opposing faces of two bones to be fused together is disclosed. The implant can include a spacer, a fusion plate, and a plurality of fasteners. The spacer can include a forward portion, a rearward portion, a top portion, a bottom portion, and two side portions, with the rearward portion including at least one cavity. The fusion plate can be as described above, and can be configured to fit within the cavity in the rearward portion of the spacer and couple together with the spacer. The fasteners can extend through the fastener bores and extend out of the second opening so that the fasteners can couple the implant to an endplate of the bone segment. As described above, the angles at which the fasteners extending through the fastener bores can be positioned is restricted due to the configuration of the fastener bores.

This summary provides only a general outline of some aspects of the technology disclosed herein. The above and other aspects of the technology of the present application will be apparent after consideration of the Detailed Description and Figures herein. It is to be understood, however, that the scope of the application shall be determined by the claims as issued and not by whether given subject matter addresses any or all issues noted in the Background or includes any features or aspects highlighted in the Summary.

BRIEF DESCRIPTION OF THE DRAWINGS

Various examples of the present invention will be discussed with reference to the appended drawings. These drawings depict only illustrative examples of the invention and are not to be considered limiting of its scope.

DETAILED DESCRIPTION

The technology of the present patent application will now be explained with reference to various Figures and the like. While the technology of the present application is described with respect to anterior lumbar interbody fusion (ALIF) implants, one of ordinary skill in the art would recognize on reading the disclosure that the technology is applicable to other implants used in spinal fusion. For example, the technology as described herein may be used for lateral interbody fusion implants, transforaminal lumbar interbody fusion (TLIF) implants, anterior cervical discectomy (ACD) implants, and posterior lumbar interbody fusion (PLIF) implants. Similarly, one of ordinary skill in the art would recognize on reading the disclosure that the technology is not limited to spinal fusion and can be applicable to other skeletal fusions, such as long bones or the like. Moreover, the technology of the present patent application will be described with reference to certain exemplary embodiments herein. The word "exemplary" is used herein to mean "serving as an example, instance, or illustration." Any embodiment described herein as "exemplary" is not necessarily to be construed as preferred or advantageous over other embodiments or examples absent a specific indication that such an embodiment or example is preferred or advantageous over other embodiments. Moreover, in certain instances, only a single "exemplary" embodiment is provided. A single example is not necessarily to be construed as the only embodiment. The detailed description includes specific details for the purpose of providing a thorough understanding of the technology of the present patent application. However, on reading the disclosure, it will be apparent to those skilled in the art that the technology of the present patent application may be practiced with or without these specific details. In some descriptions herein, generally understood structures and devices may be shown in diagrams to aid in understanding the technology of the present patent application without obscuring the technology herein.

Figure 1:
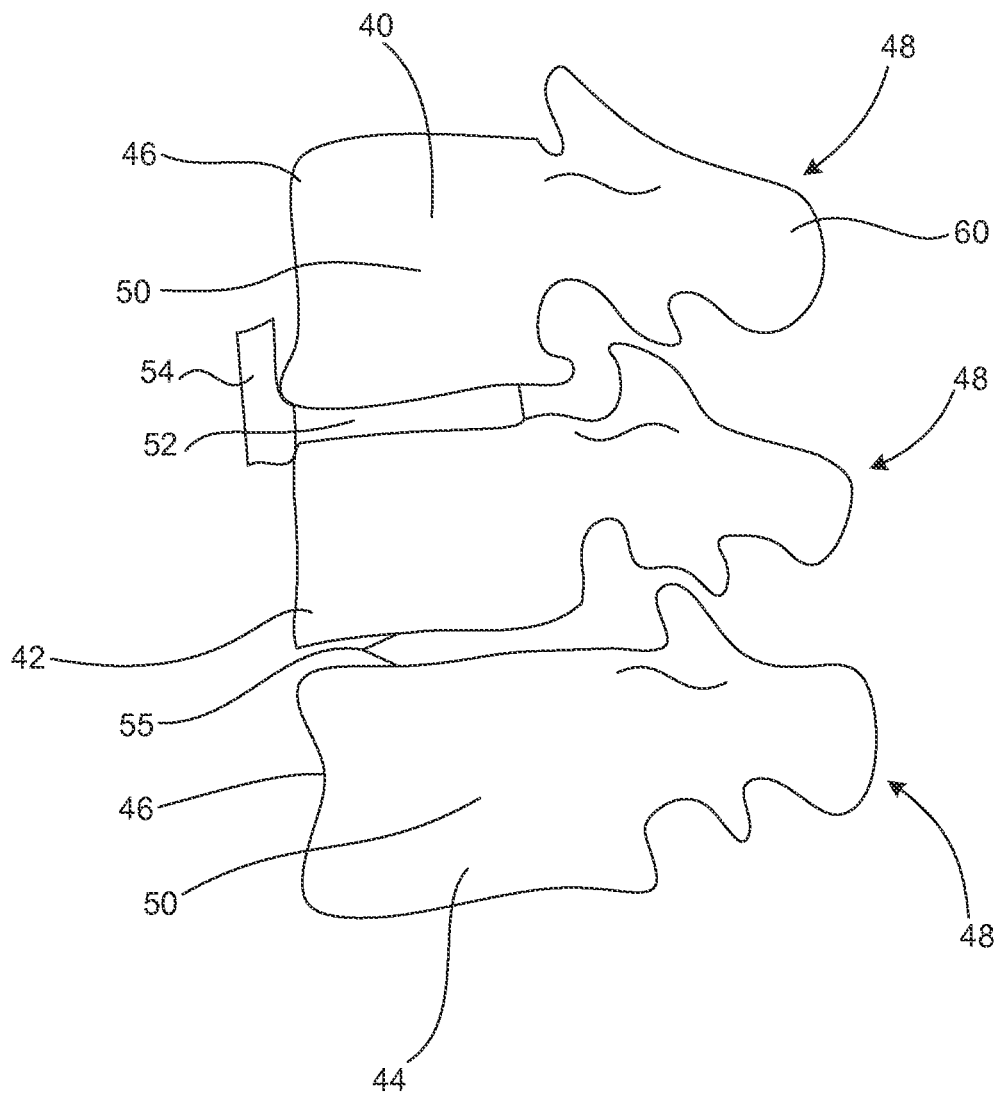
FIG. 1 is a side view of three adjacent vertebra having an implant consistent with the technology of the present application.

Referring first to FIG. 1, three vertebrae 40, 42, and 44 are provided. Each of the vertebrae 40, 42, and 44 have an anterior side 46, a posterior side 48 and lateral sides 50 (only one shown). The three vertebrae 40, 42, and 44 each have a spinous process 60.

In a normal spine, discs would reside between each of the endplates 55 of vertebrae 40 and 42, and vertebrae 42 and 44. The endplates 55 form opposed bony surfaces for spinal application, but use of the technology to be described herein is applicable to any bony segments to be fused across opposed facing bony surfaces. For convenience of illustration, the discs are not included in the Figures. However, injury, age, or other trauma may cause the discs to degenerate for one reason or another. To restore proper height to a disc, for example, a surgeon would remove all or a portion of the disc and replace it with a spacer. For example, as shown in FIG. 1, a spacer 52 may be surgically implanted in the space between vertebrae 40 and 42. As shown, spacer 52 is implanted from the anterior side of the patient. A fusion plate 54, as will be explained further below, is coupled to the spacer 52 and extends over only one of the vertebrae 40 and 42 in the exemplary embodiment of the technology shown in FIG. 1. While shown in a spinal application, the technology of the present application is usable to facilitate the fusion of other bones.

Figure 2:
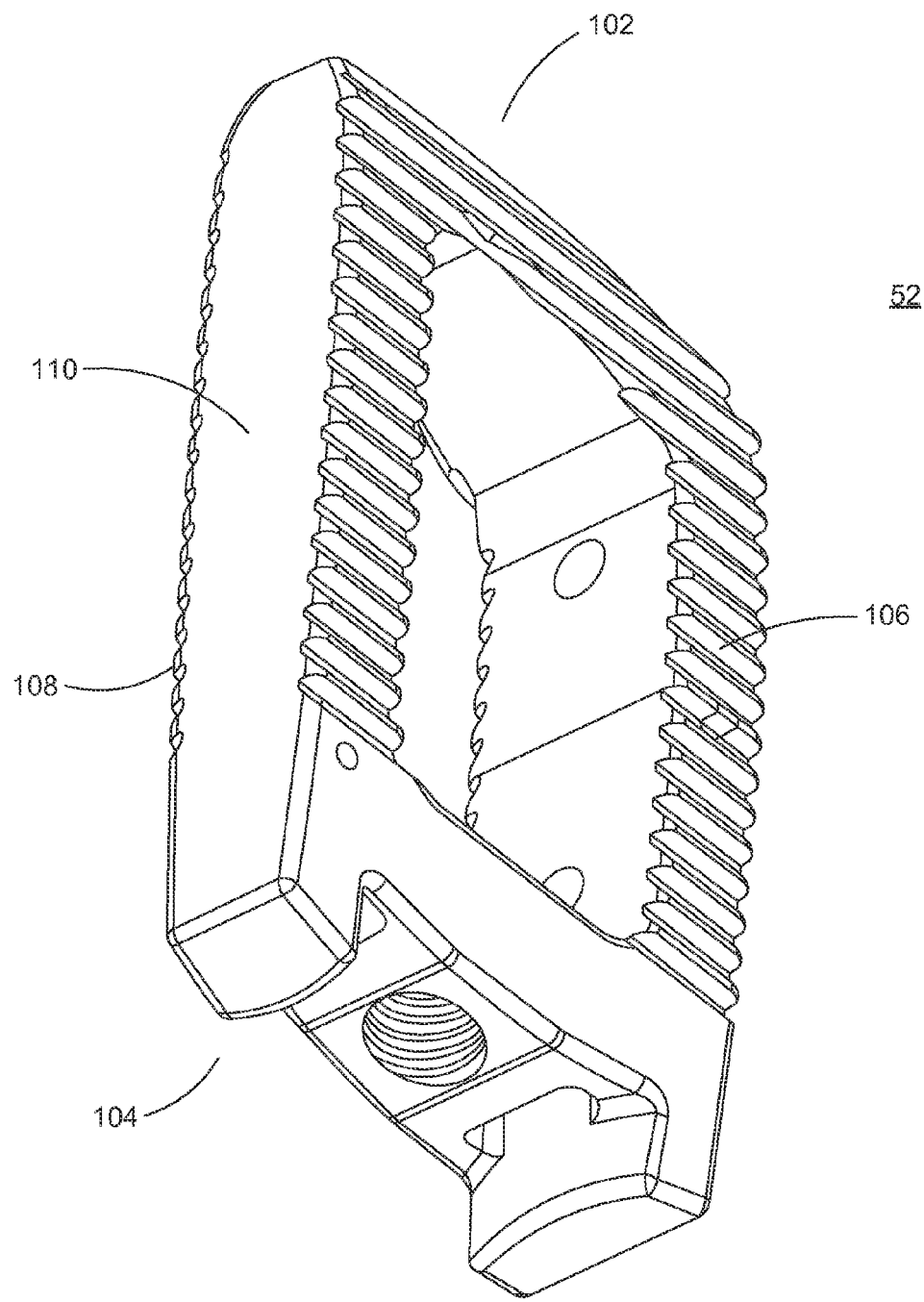
FIG. 2 is a perspective view of a spacer consistent with the technology of the present application.
Figure 3:
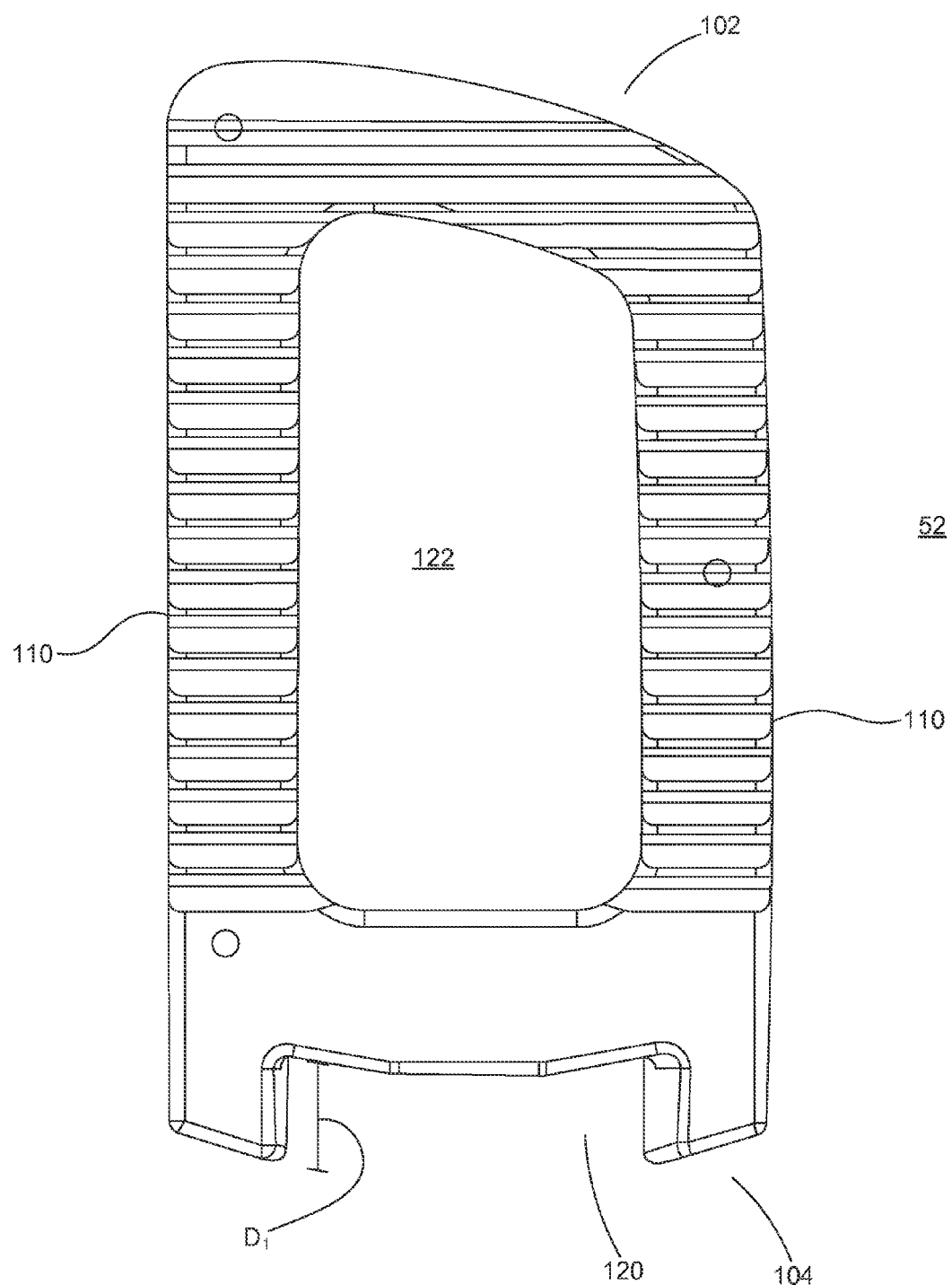
FIG. 3 is a top plan view of the spacer of FIG. 2.

Referring now to FIGS. 2 and 3, an exemplary spacer 52 is shown. The spacer 52 is generally shaped to fit within the intervertebral space and has a forward portion 102, which may be referred to as a posterior portion 102, a rearward portion 104, which may be referred to as an anterior portion 104, a top portion 106, which may be referred to as a superior portion 106, a bottom portion 108, which may be referred to as an inferior portion 108, and side portions 110. Notice that the orientation of the front (posterior), rear (anterior), left, right, top (superior), and bottom (inferior), or the like are provided for reference and should not be construed to limit the technology of the present application. The spacer 52 is provided to fit entirely in the intervertebral space, although in certain embodiments, the rearward portion 104 may extend beyond the anterior ends of the vertebrae.

The rearward portion 104 of the spacer 52 can comprise a cavity 120 having a depth $D_1$ to receive a fusion plate as will be explained further below. The spacer 52, as shown, has a void 122 providing the spacer 52 with a vaguely "D" shape. Other shapes and types of spacers 52 are possible, such as, for example, other fusion cages, dowels, and the like. The void 122 may be packed with material to facilitate bone growth and fusion of the vertebrae 40, 42. The void 122 is generally greater than 20% of the surface area of the spacer 52. Alternatively to the large void 122, a large number of smaller bone growth channels are possible.

Figure 4:
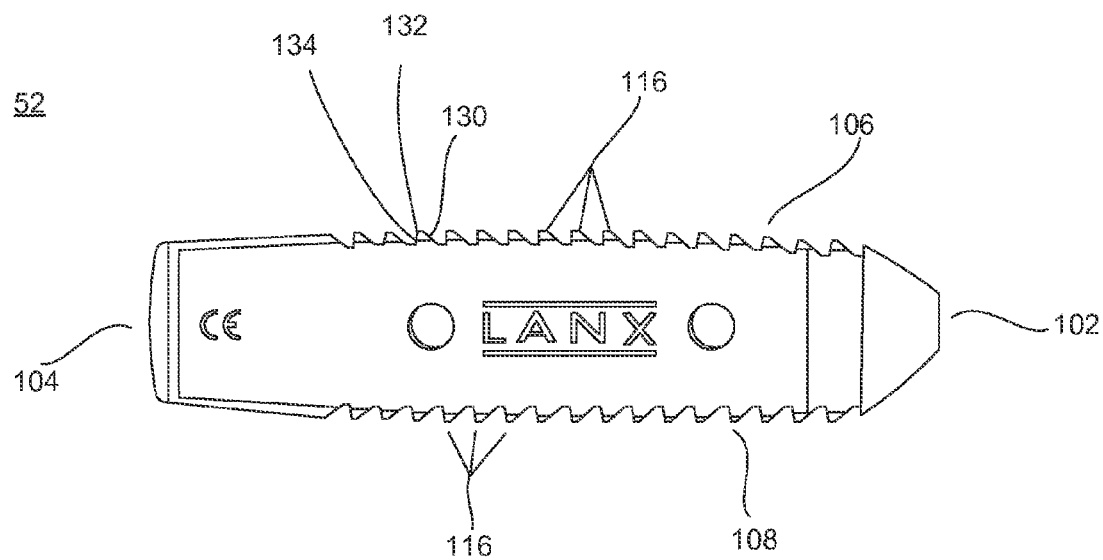
FIG. 4 is a side view of the spacer of FIG. 2.

A number of protrusions 116 may be provided on the top portion 106, the bottom portion 108, or a combination thereof. As best seen in FIG. 4 the protrusions 116 form a generally shark-tooth shape that angles from the forward portion 102 towards the rearward portion 104. The protrusions 116 generally resist movement of the spacer 52 out of the intervertebral space between vertebrae 40, 42.

Still with reference to FIG. 4, the protrusions 116 are formed by a first surface 130 forming an obtuse angle with a surface of the spacer 52. The first surface 130 extends to an engaging surface 132 of the protrusion 116. The engaging surface 132 is adapted to engage the endplates of the vertebrae 40, 42. The engaging surface 132 may be formed to a line contact, a point contact, or to a flat or convex surface formed generally parallel to the body surface. In particular, the engaging surface 132 may be formed and shaped to conform to the anatomical shape of the associated endplates. A surface formed by connecting the engaging surface 132 on the top and bottom portion 106, 108, may be shaped to conform to the anatomical shape of the associated endplates as well. A second surface 134 extends from the engaging surface 132 back to the surface of the spacer 52. The second surface 134 also forms an obtuse angle, but may form a right angle or be slightly undercut. The protrusions 116 are generally of a unified construction with the body. The protrusions 116 generally extend over the entire superior and inferior surface of the implant.

Figure 5:
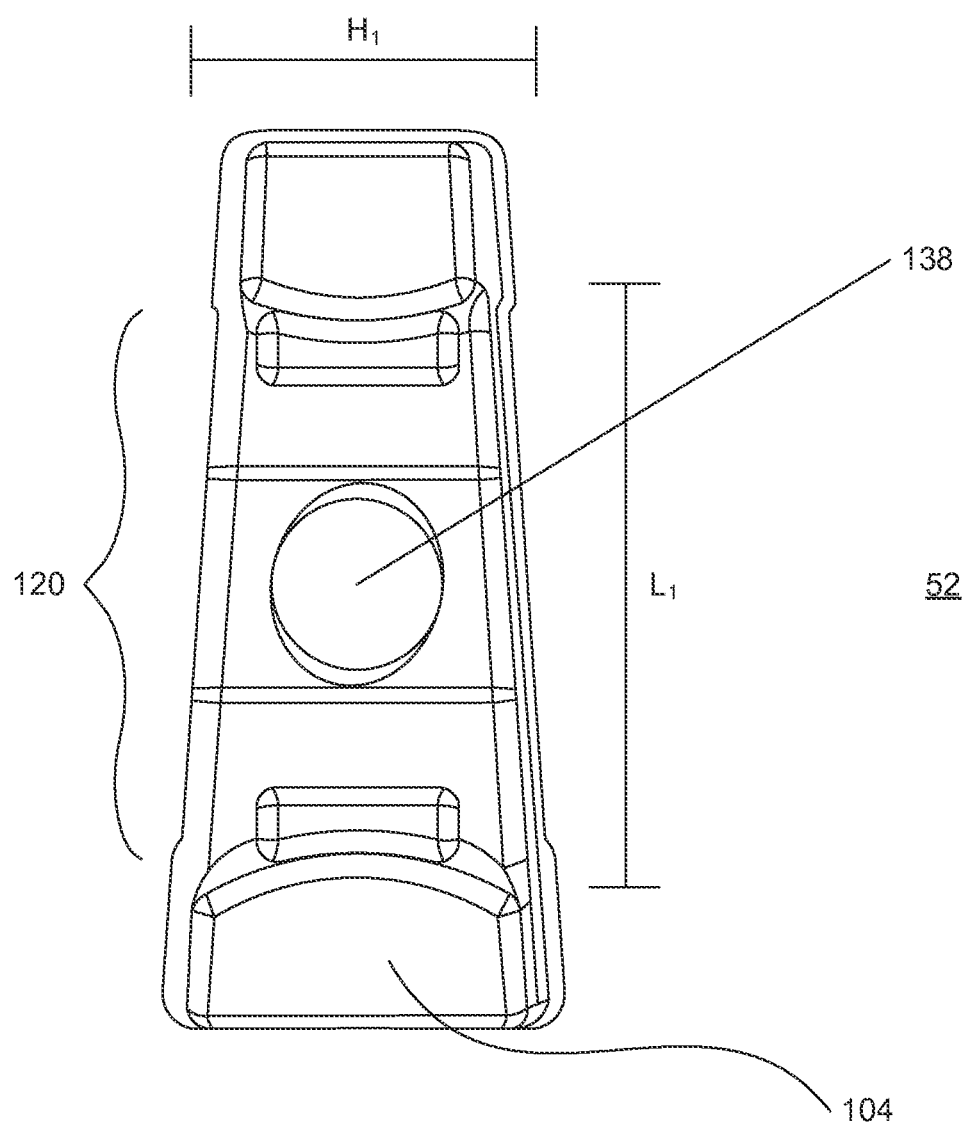
FIG. 5 is a rearward portion elevation view of the spacer of FIG. 2.

Referring now to FIG. 5, an elevation view of the rearward portion 104 of spacer 52 is provided. Cavity 120 has a length $L_1$ and a height $H_1$, and is sized to cooperatively engage a fusion plate, which will be explained further below. A threaded spacer bore 138 is in the cavity 120. The threaded spacer bore 138 is used, as will be explained further below, to couple the spacer 52 and the fusion plate. The threaded spacer bore 138 may have an undercut. The threaded spacer bore 138 can have a first thread.

As can be appreciated on reading the above, the spacer 52 is provided with a length $L_1$ and a height $H_1$ to provide an implant having a reasonably low profile to fit within the intervertebral space with the spacing desired by the surgeon. To anchor the spacer 52 to the superior and inferior vertebrae, a fusion plate 54 (FIG. 1) is provided in certain aspects of the technology of the present application. Ideally, the plate provided has as low a profile as possible.

Figure 6:
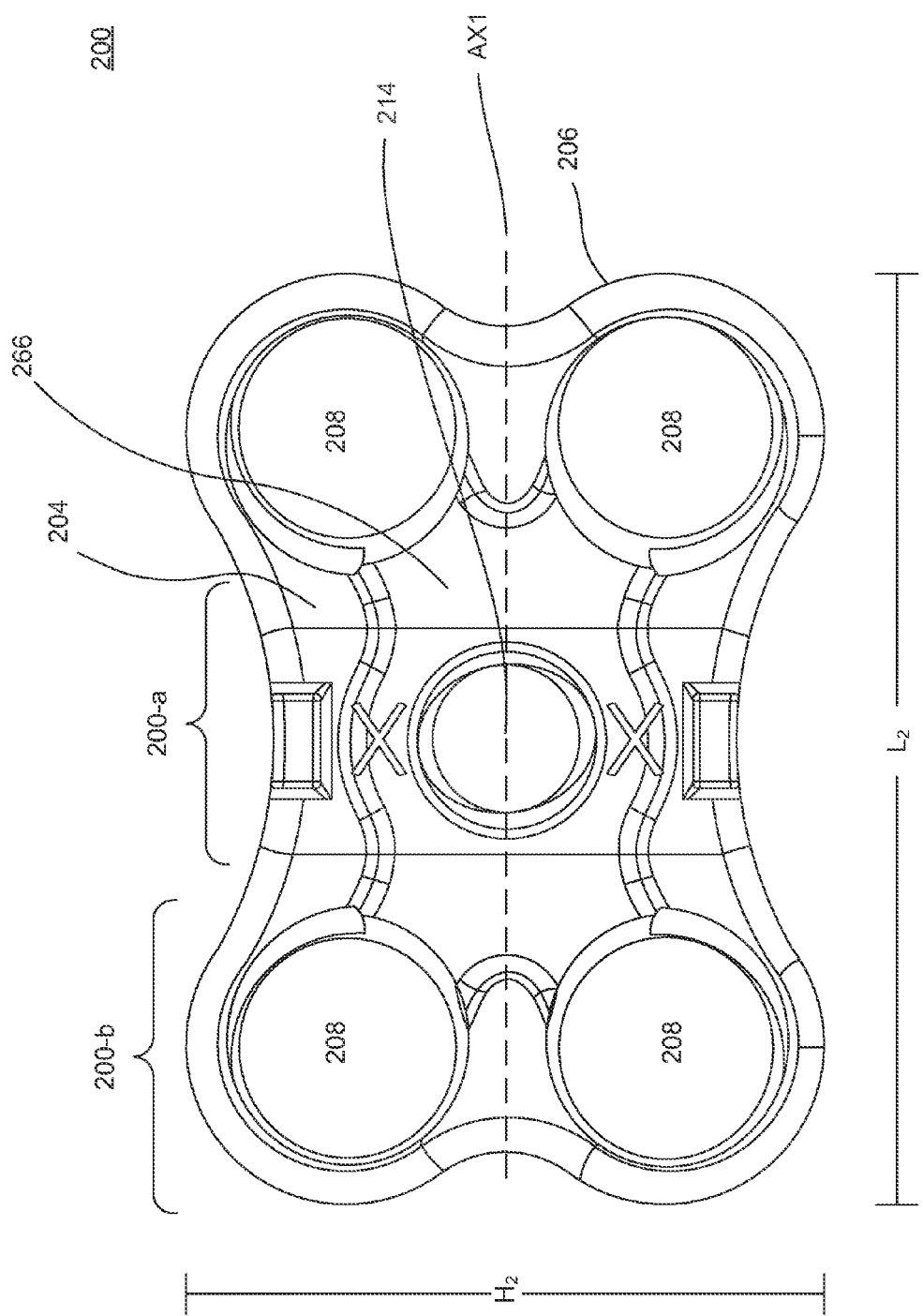
FIG. 6 is a top plan view of a fusion plate consistent with the technology of the present application.
Figure 7:
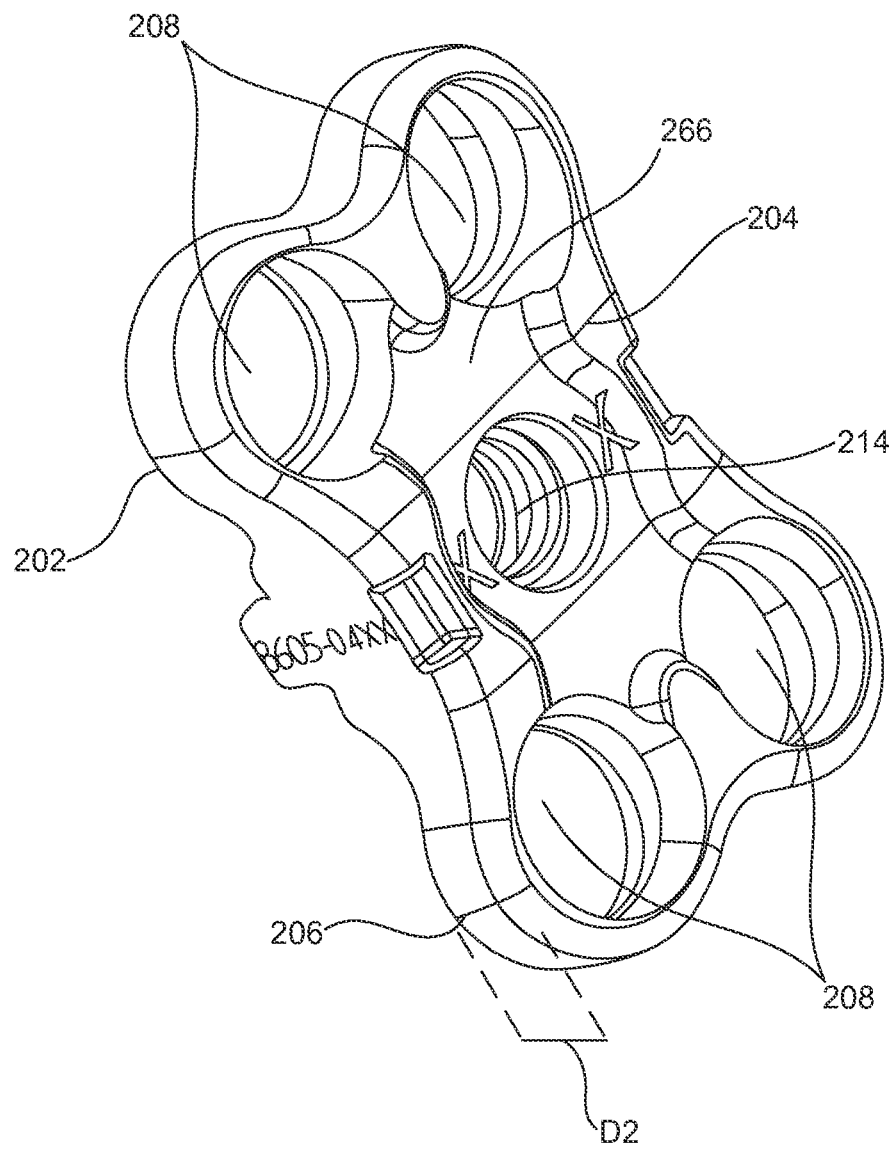
FIG. 7 is a perspective view of a fusion plate consistent with the technology of the present application.

Referring now to FIGS. 6 and 7, a fusion plate 200 consistent with the technology of the present application is provided. The fusion plate 200 has a forward face 202 and a rearward face 204 opposite the forward face 202. A sidewall 206 extends between the forward face 202 and the rearward face 204. The edges of sidewall 206 may be beveled or chamfered to reduce trauma. The fusion plate 200 has a length $L_2$, a height $H_2$, and a depth $D_2$ to allow fusion plate 200 to cooperatively fit in cavity 120.

The fusion plate 200 can include a main body 200-a and one or more extension side portions 200-b. The main body portion 200-a can include a plate bore 214 (described in greater detail below) which can be used to couple the fusion plate 200 to the spacer 52. The one or more extension side portions 200-b extend off of and away from the main body portion 200-a. In some embodiments, the fusion plate includes two extension side portions 200-b which extend away from opposite sides of the main body 200-a. When the fusion plate 200 is coupled with the spacer 52, the extension side portions 200-b can be adapted to extend above or below the height $H_1$ of the spacer 52. In some embodiments, the extension side portions 200-b are aligned so that the rearward face 204 of the main body portion 200-a and the extension side portions 200-b lie in generally the same plane. In other embodiments, the extension side portions 200-b can extend away from the main body 200-a at an angle.

Figure 15:
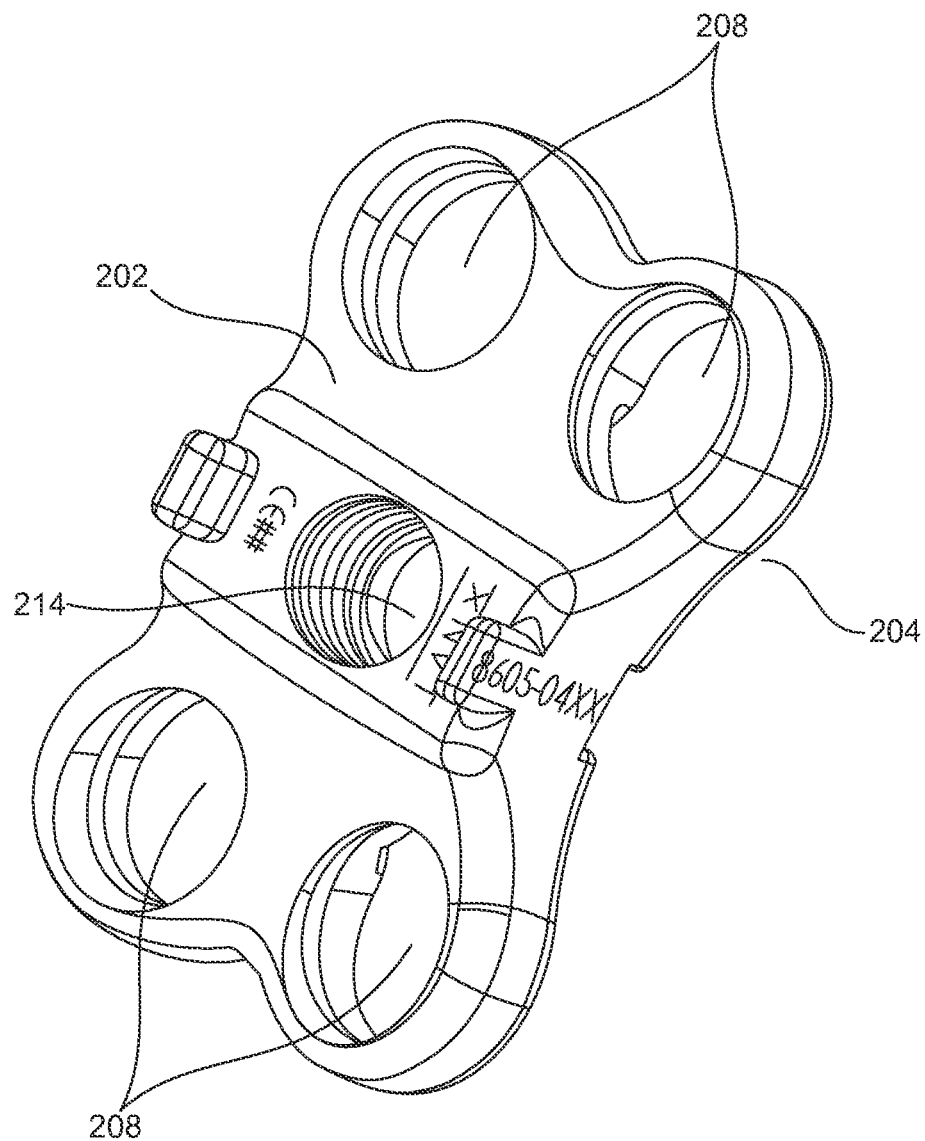
FIG. 15 is a perspective view of the forward face of a fusion plate consistent with the technology of the present application.

With reference now to FIGS. 6, 7 and 15, the extension side portion 200-b includes one or more fastener bores 208. The fastener bores 208 extend from the rearward face 204 through to the forward face 202 and provide an opening 208-a in the rearward face 204 and an opening 208-b in the forward face 202. The fastener bores 208 are adapted to receive a fastener which can extend through the fastener bore 208 and secure the fusion plate 200 to a bone, such as a vertebral body.

Each extension side portion 200-b can include one or more fastener bores 208. Where more than one extension side portion 200-b is present, each extension side portion 200-b can include the same number of fastener bores 208. Each extension side portion 200-b could also include a different number of fastener bores 208. In some embodiments where more than one extension side portion 200-b is present and each extension side portion includes the same number of fastener bores 208, the extension side portions 200-b and fastener bores 208 can be set up as a mirror image of one another. In other embodiments, the fastener bores 208 on opposing extension side portions 200-b can be arranged non-symmetrically. As shown in FIGS. 6, 7, and 15, one embodiment includes two extension side portions 200-b extending from opposing sides of the main body 200-a and which include the same number of fastener bores 208 (in this case, two each) aligned in a generally symmetrical fashion.

In some embodiments, the fastener bores 208 are adapted to restrict the direction in which a fastener inserted in the fastener bore 208 can pivot or be angled. Generally speaking, the diameter of the fastener bore 208 is slightly larger than the diameter of the fastener. This allows a fastener inserted into the fastener bore 208 to pivot 360 degrees around the fastener bore 208 and be positioned at various angles other than parallel to the axis of the fastener bore. This directional freedom can be desirable to a user, as it allows a surgeon to select a specific angle at which the fastener can be driven in to a bone. However, there are also drawbacks to this amount of directional freedom. One specific example where directional freedom can be a drawback is that it permits human error, such as allowing a user to drive a fastener in a direction that results in the fastener coming in to contact with and damaging nerves or vessels adjacent the bone rather than the bone itself.

Accordingly, in some embodiments, the fastener bores 208 are dimensioned to restrict the directions in which a fastener can be angled once inserted into the fastener bore 208. The direction in which the fastener is restricted from moving is generally not limited and can be selected based on the specific use/surgical procedure.

Figure 8:
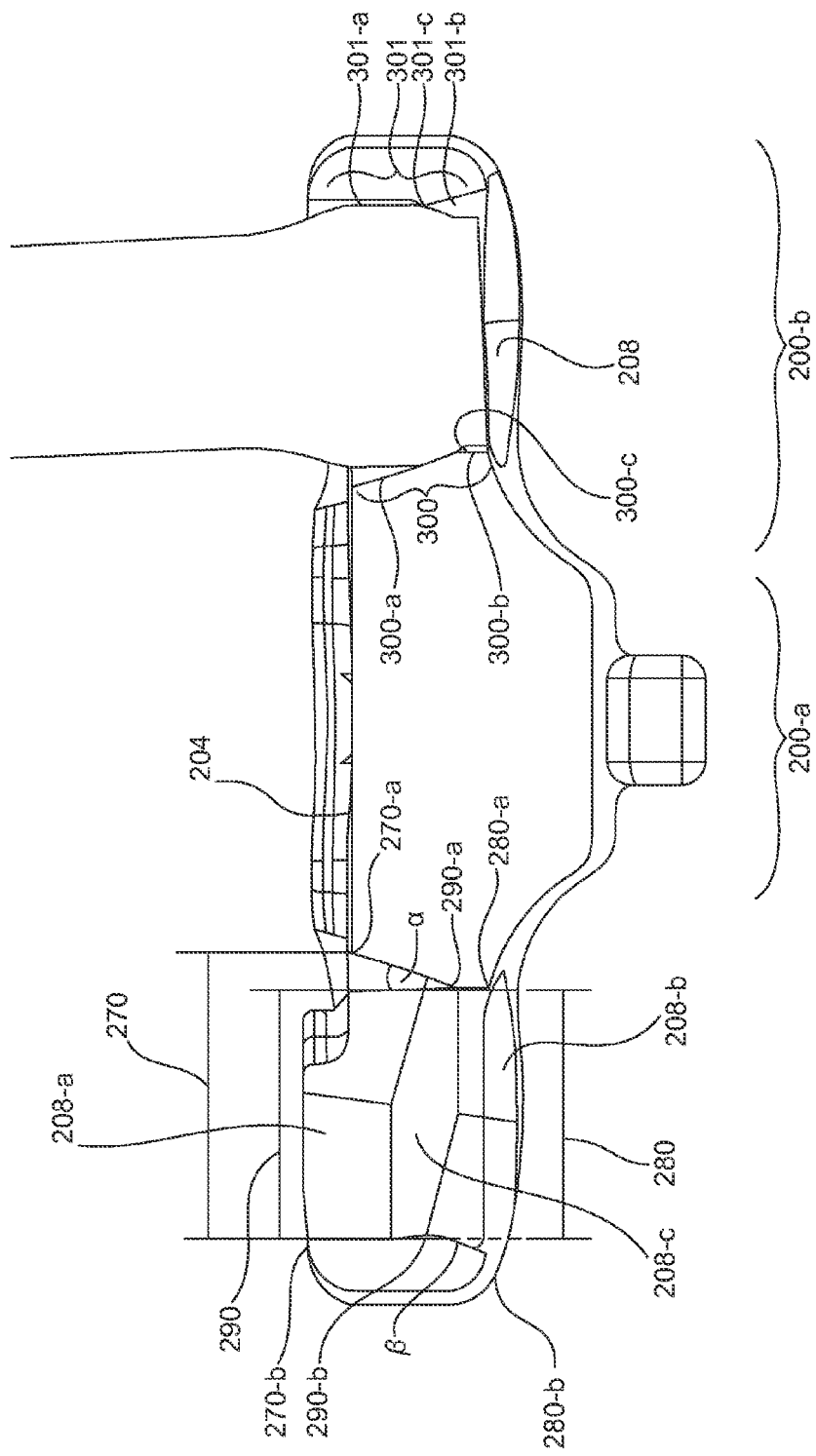
FIG. 8 is a cross sectional view of a fusion plate consistent with the technology of the present application.
Figure 9A:
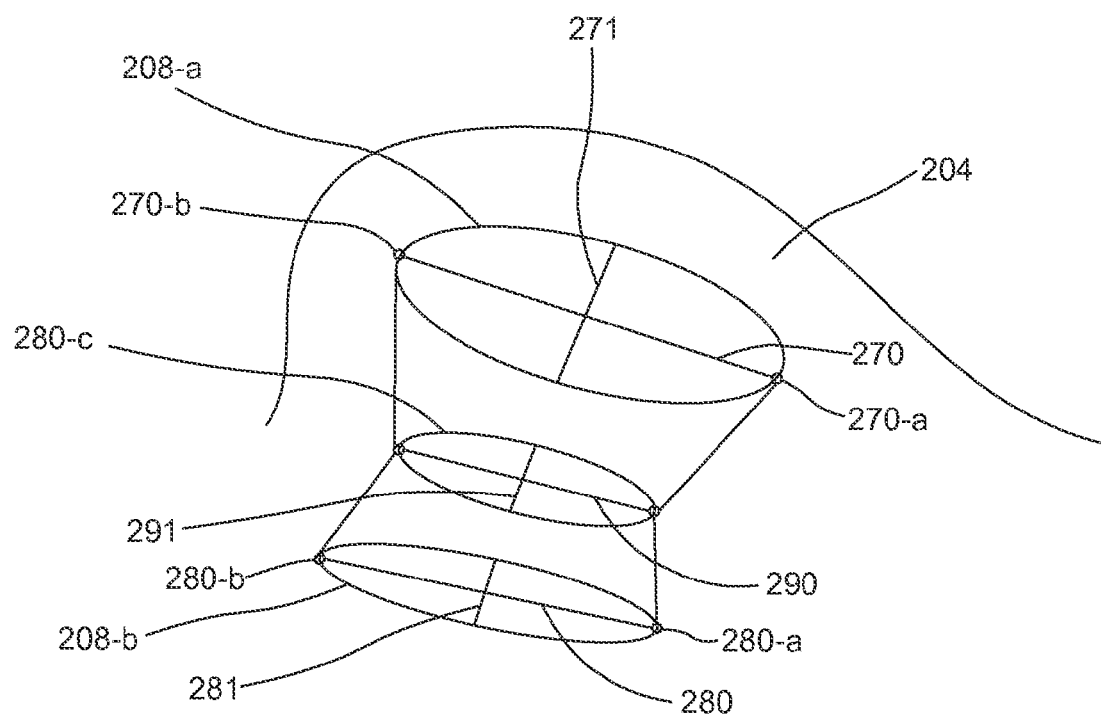
FIG. 9A is a perspective view of a fastener bore in a fusion plate consistent with the technology of the present application.
Figure 9B:
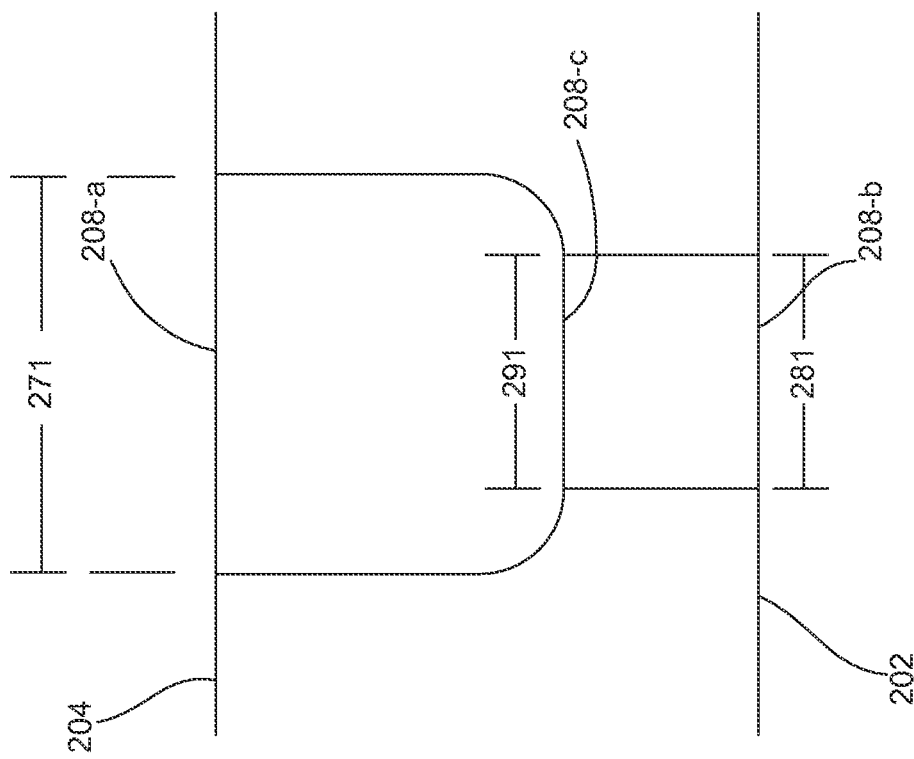
FIG. 9B is a cross sectional view of a fastener bore from a view perpendicular to the view shown in FIG. 8.

With reference to FIGS. 8, 9A and 9B, a fastener bore 208 capable of restricting movement of a fastener inserted therethrough can generally include a first opening 208-a, a second opening 208-b, and a throat area 208-c located intermediate the first opening 208-a and the second opening 208-b. The first opening 208-a includes a first diameter 270 extending from a side of the first opening 208-a closest to the main body 200-a to an opposing side of the first opening 208-a. The second opening 208-b includes a second diameter 280 extending from a side of the second opening 208-b closest to the main body 200-a to an opposing side of the second opening 208-b. The throat portion 208-c includes a third diameter 290 extending from a side of the throat portion closest to the main body 200-*a* to an opposing side of the throat portion 208-*c*. In some embodiments, the length of the third diameter 290 is shorter than the length of the first diameter 270 and the second diameter 280 such that the bore 208 has a generally hourglass shape.

The third diameter 290 will generally have a length that is only slightly larger than the diameter of the fastener inserted into the bore 208. The first diameter 270 and the second diameter 280 are larger than the diameter of the fastener so that the head of the fastener can move about the area above the throat portion 208-*c* and the distal end of the fastener opposite the head can move about the area below the throat portion 208-*c*, with the throat portion 208-*c* serving as a fulcrum.

With reference to FIGS. 9A and 9B, the first opening 208-*a* includes a fourth diameter 271 that is perpendicular to the first diameter 270. The second opening 208-*b* includes a fifth diameter 281 that is perpendicular to the second diameter 280. The throat portion 208-*c* includes a sixth diameter 291 that is perpendicular to the third diameter 290. In some embodiments, the length of the fifth diameter 281 is approximately equal to the sixth diameter 291. The length of the fifth diameter 281 and the sixth diameter 291 is approximately equal to the diameter of the fastener body. The length of the fourth diameter 271 is longer than the fifth diameter 281 and the sixth diameter 291 and is approximately equal to the diameter of the fastener head.

Based upon the above described configuration for the first diameter 270, second diameter 280, third diameter 290, fourth diameter 271, fifth diameter 281, and sixth diameter 291, a fastener inserted through the bore 208 is capable of being pivoted in a direction parallel to the longitudinal axis AX1 shown in FIG. 6 (by virtue of the space provided above and below the throat portion 208-*c* in that direction) but is restricted from being pivoted in a direction perpendicular to the longitudinal axis AX1 (by virtue of the absence of space above and below the throat portion 208-*c* in that direction). Accordingly, the user is free to pick a variety of angles for the fastener in a direction parallel to the longitudinal axis AX1 but is prevented from positioning the fastener at an angle that is perpendicular to the longitudinal axis AX1. This provides the user with some directional freedom, but not in a direction that could result in damage to, for example, nerves and vessels located adjacent the vertebral body.

In some embodiments, first opening 208-*a* is offset from the second opening 208-*b*. With reference to FIG. 8, the first diameter 270 of the first opening 208-*a* can include a first end 270-*a* that is proximate the main body 200-*a* and a second end 270-*b* opposite the first end 270-*a*, while the second diameter 280 of the second opening 208-*b* has a first end 280-*a* that is proximate the main body 208-*a* and a second end 280-*b* that is opposite the first end 280-*a*. In some embodiments, the first end 270-*a* of the first diameter 270 is closer to the main body 200-*a* than the first end 280-*a* of the second diameter 280. In some embodiments, the second end 270-*b* of the first diameter 270 is closer to the main body 200-*a* than the second end 280-*b* of the second diameter 280. This configuration results in a first opening 208-*a* and a second opening 208-*b* that are not aligned on top of each other. Instead, the first opening 208-*a* is offset from the second opening 208-*b*.

With continuing reference to FIG. 8, in some embodiments, fastener bore 208 includes a first side wall portion 300 proximate the main body 200-*a* and a second side wall portion 301 opposite the first side wall portion 300. The first side wall portion 300 can include an angled section 300-*a* and a vertical section 300-*b*. The angled section 300-*a* extends from the first opening 208-*a* to a point 300-*c* intermediate the first opening 208-*a* and the second opening 208-*b*. The vertical section 300-*b* extends from the intermediate point 300-*c* to the second opening 208-*b*. The vertical section 300-*b* is vertical relative to the rearward and forward face of the fusion plate 200, while the angled section 300-*a* forms an angle ALPHA with the vertical section 300-*b*. The second side wall portion 301 can include a vertical section 301-*a* and an angled section 301-*b*. The vertical section 301-*a* extends from the first opening 208-*a* to a point 301-*c* intermediate the first opening 208-*a* and the second opening 208-*b*. The angled section 301-*b* extends from the intermediate point 301-*c* to the second opening 208-*b*. The vertical section 301-*a* is vertical relative to the rearward and forward face of the fusion plate 200, while the angled section 301-*b* forms an angle BETA with the vertical section 300-*a*. In some embodiments, the intermediate point 300-*c* is closer to the forward face of the fusion plate 200 than the intermediate point 301-*c*.

In some embodiments, the angle ALPHA is equal to the angle BETA and the angled section 300-*a* is parallel to the angled section 301-*b*. In some embodiments, the angle of the angled section 300-*a* and 301-*b* sets a maximum angle at which the fastener can be angled when inserted in the fastener bore 208.

The above described configuration for the fastener bore 208 can be rotated any number of degrees in order to change the direction in which movement of the fastener is restricted. For example, rotating the above described fastener bore 90 degrees would limit the movement of the fastener so that it can be pivoted in a direction perpendicular to the longitudinal axis AX1 of the fusion plate, but not in a direction parallel to the longitudinal axis AX1 of the fusion plate.

As mentioned above and referring now to FIGS. 6, 7, and 15 the main body 200-*a* of the fusion plate 200 can further comprise a plate bore 214. The plate bore 214 is adapted to be aligned with threaded spacer bore 138. In one aspect of the technology, the fusion plate 200 is coupled to the spacer 52 using a threaded connector that extends through the plate bore 214 and the spacer bore 138 and engages with threading located on the inner walls of each.

Figure 10:
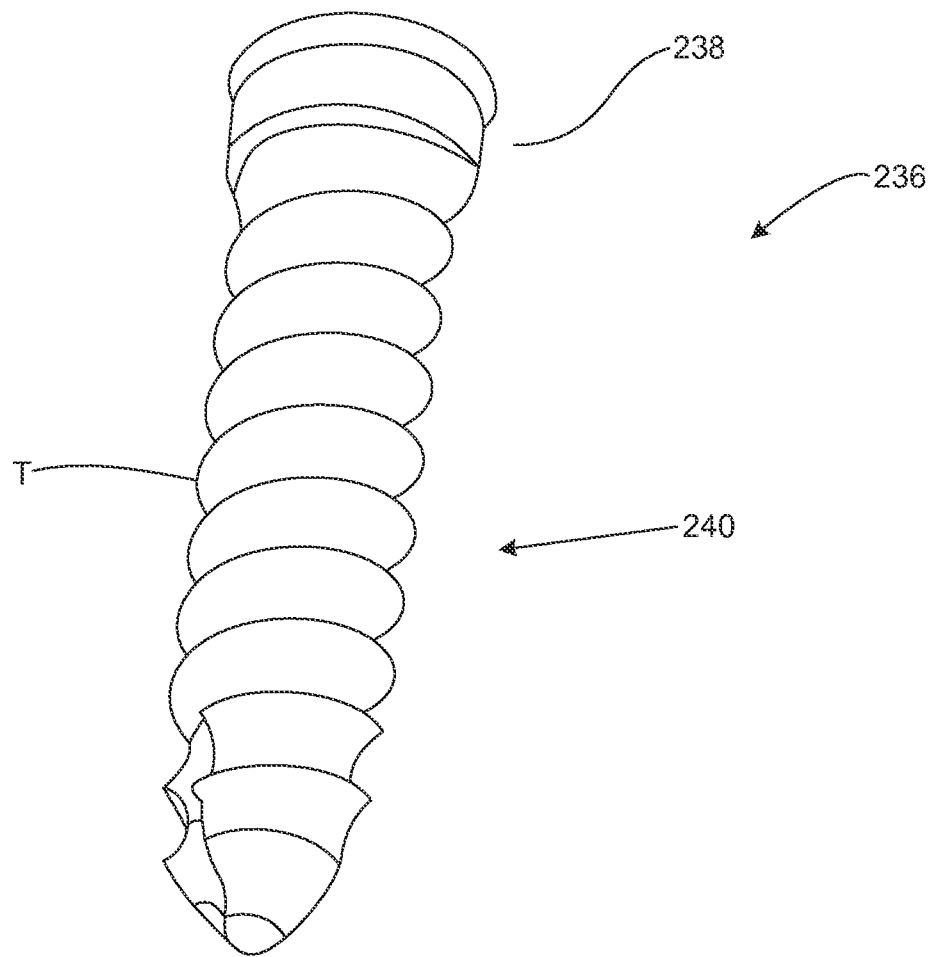
FIG. 10 is a perspective view of a fastener consistent with the technology of the present application.

With reference to FIG. 10, the spacer 52 and the fusion plate 200 are coupled to the superior and inferior vertebrae in this exemplary aspect by a plurality of fasteners 236. The fasteners 236 may be any conventional fasteners, such as, for example, a bone screw 236. The bone screw 236 may comprise a head 238 and a shaft 240 having threads T. The fasteners 236 are adapted to be threaded into the endplates of the vertebrae 40, 42 by extending the fasteners through the fastener bores 208. The fastener bores 208 described herein are configured to allow the fasteners to be positioned at various angles to provide greater flexibility with respect to the best direction in which the fasteners can be inserted into the bone to ensure a secure coupling between the implant and the bone.

Figure 16:
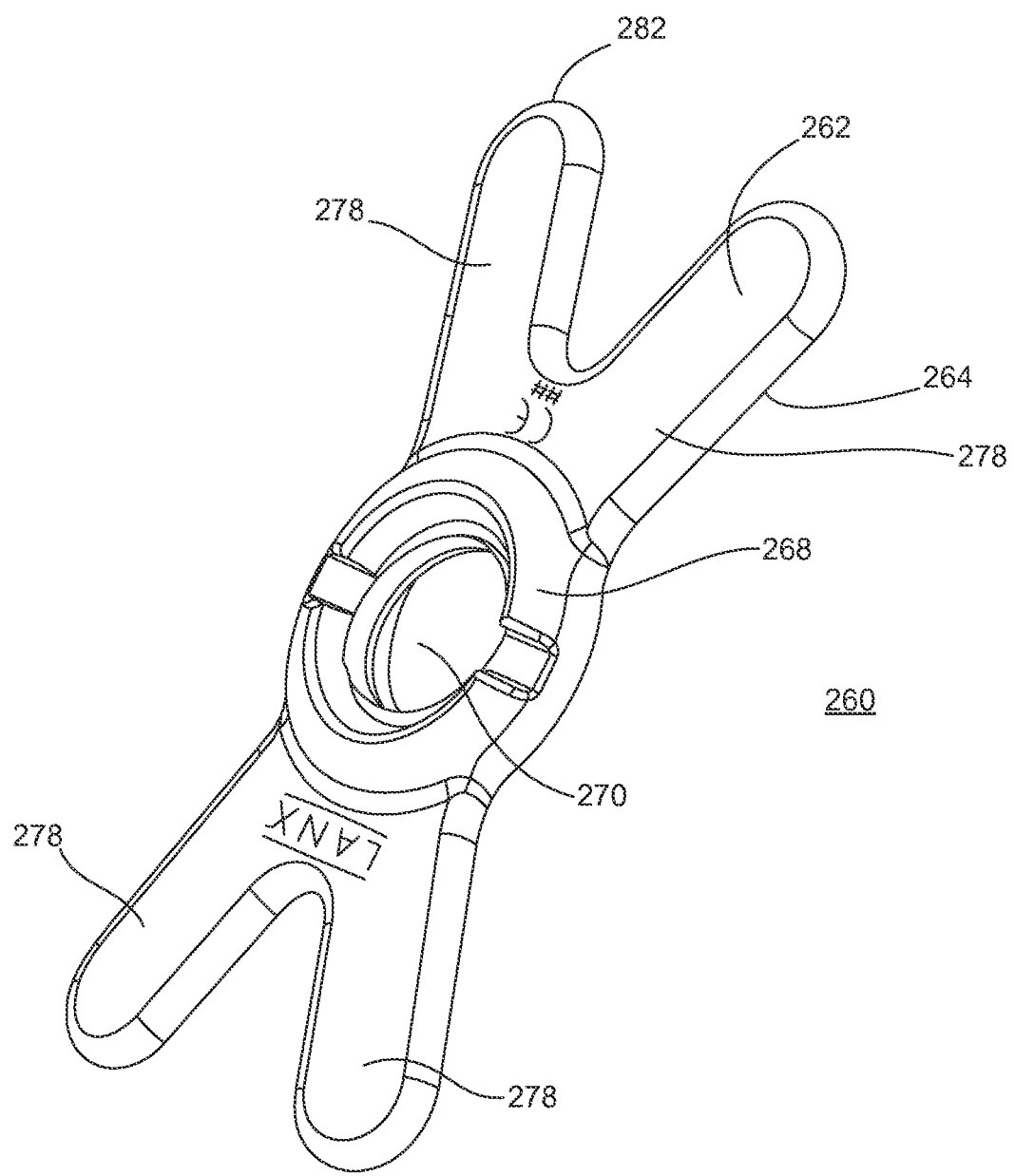
FIG. 16 is a perspective view of a cover plate consistent with the technology of the present application.

The fasteners 236, as is conventionally known, have a tendency to reverse thread or back-out of the vertebrae 40, 42, and the fusion plate 54. A lock may be provided to inhibit the fasteners 236 from reverse threading. In certain aspects of the technology, the lock may be a cover plate. Referring now to FIG. 16, a cover plate 260 is provided that is usable with the fusion plate 200. The cover plate 260 has a first face 262 and a second face 264 opposite the first face 262. The cover plate 260 may be shaped to fit into a recess 266 in the fusion plate 200, as shown in FIGS. 6 and 7. The cover plate 260, as shown, generally has a main body portion 268 with a cover plate bore 270.

A connecting pin, which will be explained further below, couples the cover plate 260 to the fusion plate 200. The cover plate bore 270 aligns with the plate bore 214 described above. A plurality of arms 278 extend from the main body portion 268. The arms 278 extend from the main body portion a sufficient distance such that at least a distal end 282 of the arm extends over fastener bore 208. The distal end 282 of the arm, thus, resists the ability of the fastener 236 to reverse thread from the implant.

As can be appreciated, the shape and size of the cover plate 260 depends in part on the shape and size of fusion plate 200. The shape and size of the cover plate 260 specifically shown in FIG. 16 is designed for use with the fusion plate 200 shown in FIGS. 6 and 7. Generally, each arm on cover plate 260 is associated with a single fastener bore 208.

Figure 11:
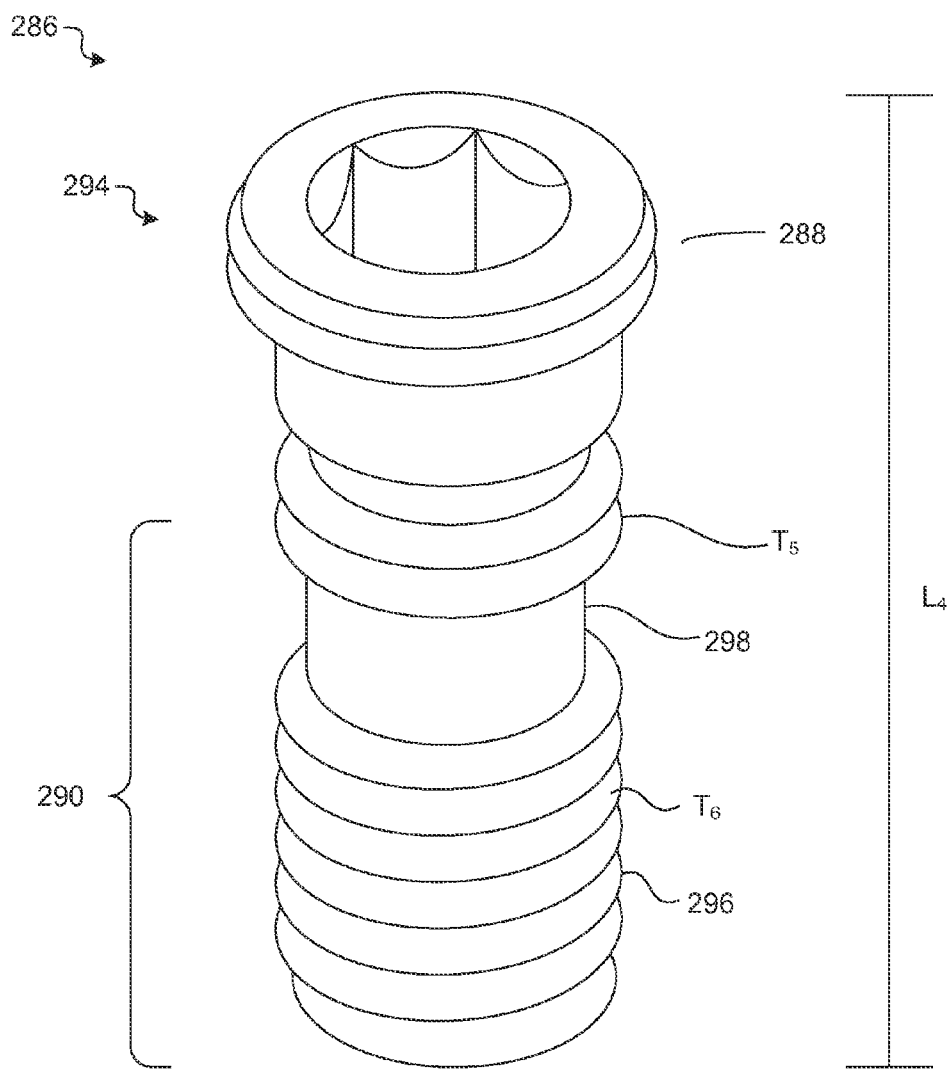
FIG. 11 is a perspective view of a connector pin consistent with the technology of the present application.

As described above, the cover plate bore 270 generally aligns with the plate bore 214. The cover plate 260 is coupled to the fusion plate 200 using a connecting pin 286 as shown in FIG. 11. The connecting pin 286 has a head 288 and a shaft 290. The shaft 290 has a proximal portion 294 proximate to the head 288, a distal portion 296 distal from the head 288, separated by a medial portion 298. The proximal portion 294 has a first thread $T_5$ that is designed to cooperatively engage the threads of the cover plate 260. The medial portion 298 is shown as being threadless and provides a transition from the proximal portion to the distal portion. The distal portion 296 has a second thread $T_6$ that is designed to cooperatively engage the threads of an inner threaded bore in the fastener used to couple the fusion plate 200 to the spacer 52. The connecting pin 286 has length $L_4$ and couples the cover plate 260 to the fusion plate 200.

Figure 17:
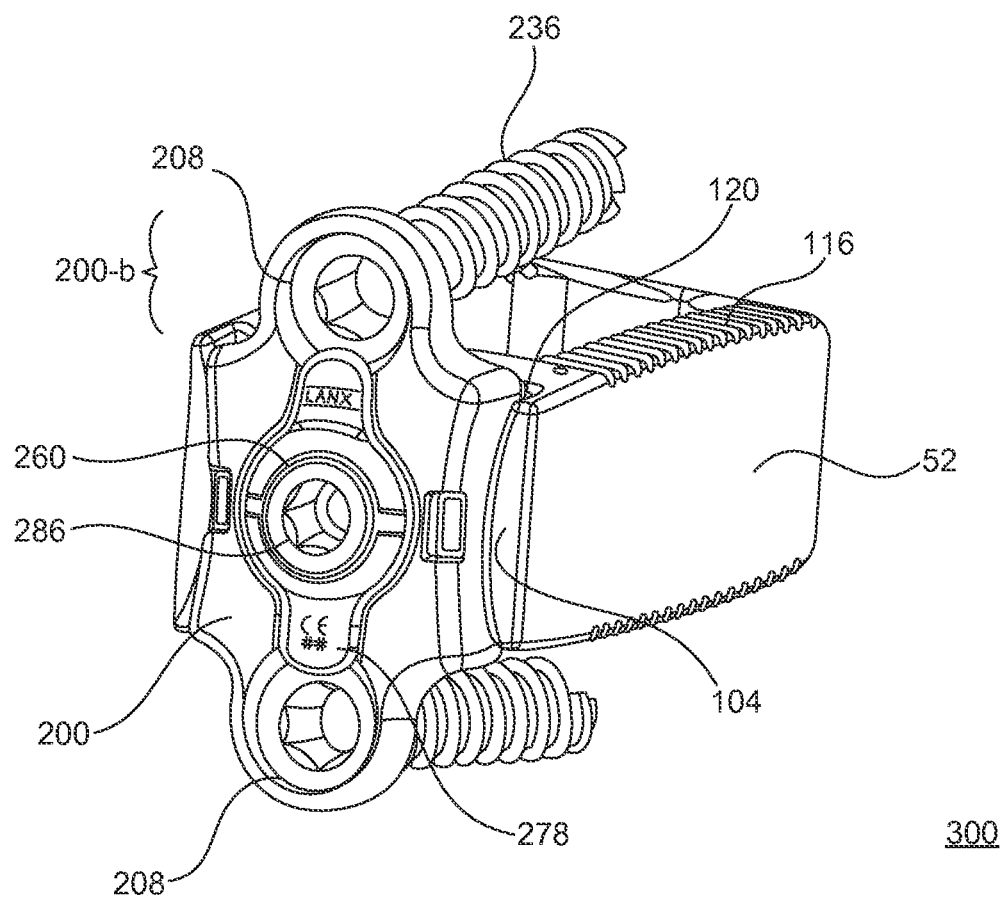
FIG. 17 is a perspective view of an implant consistent with the technology of the present application.

Referring now to FIG. 17, an implant 300 consistent with the above is provided. The implant 300 includes spacer 52. The protrusions 116 are shown on the top (or superior) portion. The cavity 120 in the rearward portion 104 has the fusion plate 200 therein. The fastener bores 208 of the fusion plate 200 are located on the extension side portions 200-b of the fusion plate. The fasteners 236 extend through the fastener bores 208 and can be positioned at a variety of angles permitted by the configuration of the fastener bores 208. The cover plate 260 is provided with arms 278 covering the fastener bores 208. The connecting pin 286 is then moved into cover plate bore 270.

In some embodiments, the fusion plate described above can be used without a spacer. In such embodiments, the fusion plate is secured to, for example, vertebral bodies using fasteners, but the fusion plate is not coupled to a spacer. In some embodiments, no spacer will be lodged between vertebral bodies when the fusion plate is secured to the vertebral bodies. In some embodiments, a cover plate can be used with the fusion plate even when the fusion plate is not used with a spacer.

The technology of the present application also includes methods for implanting the apparatus described above. While the methodology is provided in certain discrete steps, one of ordinary skill in the art will recognize that the steps identified may be broken into multiple steps or multiple steps may be combined into a single step. Moreover, the sequence of events provided may be altered or rearranged without departing from the technology of the present application.

With that in mind, the surgeon would first determine the appropriate spacer to be used. In spinal applications, the spacer may be sized to restore the height corresponding to the height of a healthy vertebra. In other applications, the spacer may be sized to most readily promote fusion or the like.

Once the appropriate spacer is identified, the surgeon may implant the spacer in the fusion site. This step may be carried out using any implanting steps known to those of ordinary skill in the art, including the use of specialized tools or instruments to implant the spacer at the fusion site. In an exemplary implantation step, the forward face of the spacer is implanted into the fusion site and the spacer is moved into the fusion site until a desired length of the spacer is implanted in the fusion site. The rearward face may jut out of the fusion site, may be flush with the bone segments, or may be inside the fusion site.

In some embodiments, the spacer is implanted with a coupling mechanism already coupled to the spacer. For example, a threaded connector may be threaded into the spacer bore prior to implanting the spacer in the fusion site. The coupling mechanism can then be used to couple a fusion plate to an implanted spacer. Alternatively, the coupling mechanism can be added to the spacer after the spacer has been implanted.

Next, a fusion plate would be selected and coupled to the spacer already implanted in the fusion site. The fusion plate can be coupled to the spacer using any mechanisms known to those of ordinary skill in the art. As noted above, a threaded connector may be used to allow the fusion plate to be snap fit to the spacer. For example, the protrusions on the slotted head may be compressed and fitted into the fusion bore until a snap fit is formed between the slotted head and the fusion plate. In other embodiments, the fusion plate is coupled to the implanted spacer, followed by using a fastener to secure the fusion plate to the spacer. A fastener can be inserted through the fusion plate bore and spacer bore, which can each include threads selected to mate with threads on the fastener.

The surgeon would next use fasteners to couple the implant to the bony segments, such as the superior and inferior vertebrae for a spinal application. The surgeon has the option of positioning the fasteners at a variety of angles permitted by the fastener bores. Likewise, the surgeon is prohibited from positioning the fasteners at various angles not permitted by the fastener bore and which ideally prevent the surgeon from causing the fasteners to contact an area other than the bone.

Figure 12:
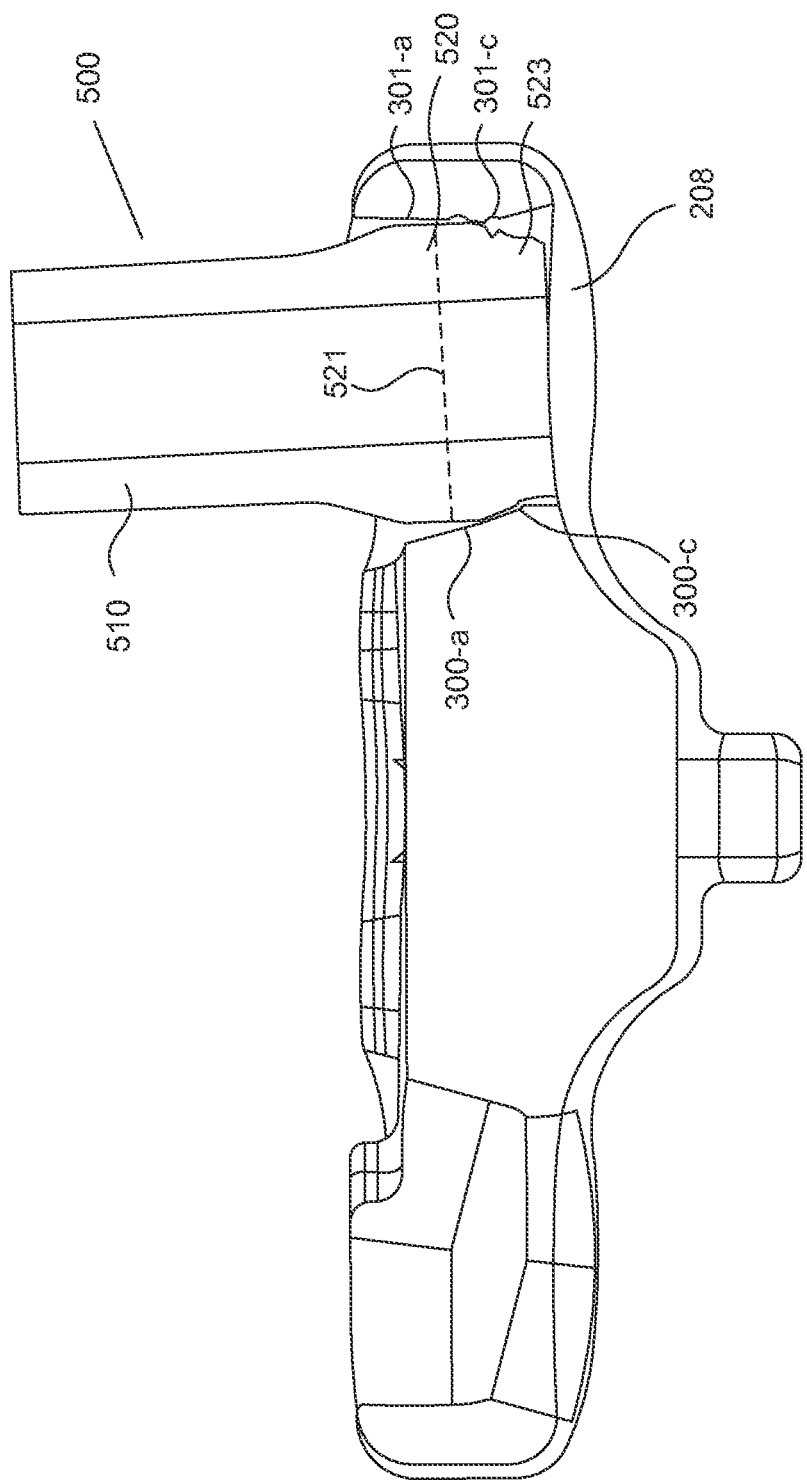
FIG. 12 is a cross sectional view of a fusion plate and fastener instrument consistent with the technology of the present application.

In some embodiments, an instrument adapted for use with the fusion plate described herein can be used in order to position and drive the fasteners into the bony segments. With reference to FIG. 12, the instrument 500 can generally include a shaft portion 510 and a fastener engagement end 520 positioned at a distal end of the shaft portion 510. In some embodiments, the fastener engagement end 520 comprises a spherical shape that is shaped and configured to mate with the fastener bore 208 and allow the instrument 500 to sweep through the range of angles permitted by the fastener bore 208. The rounded shape of the fastener engagement end 520 allows the slide back and forth along the vertical portion 301-a and the angled portion 300-a of the fastener bore 208. In some embodiments, diameter 521 of the fastener engagement end 520 is larger than a distance 522 between intermediate point 300-c and intermediate point 301-c so that the fastener engagement end 520 cannot pass completely through the fastener bore 208. Instead, the fastener engagement end 520 rests against the angled portion 300-a and the vertical portion 301-a and pivots about this area to position the fastener at a desired angle. As also shown in FIG. 12, the fastener engagement end 520 may include a distal vertical end 523 where the spherical shape straightens out at the very distal end of the instrument 500.

Figure 13:
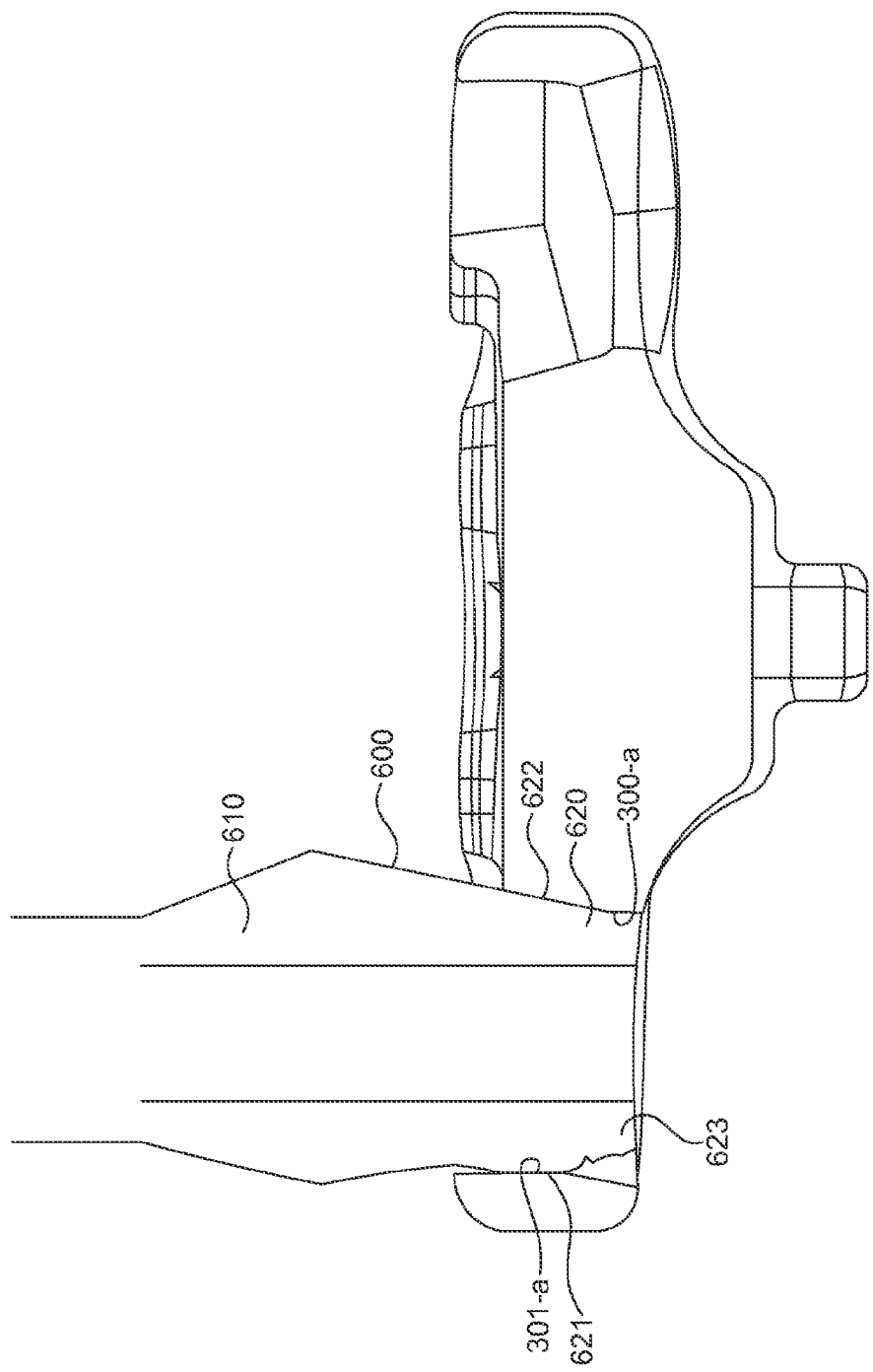
FIG. 13 is a cross sectional view of a fusion plate and fastener instrument consistent with the technology of the present application.
Figure 14:
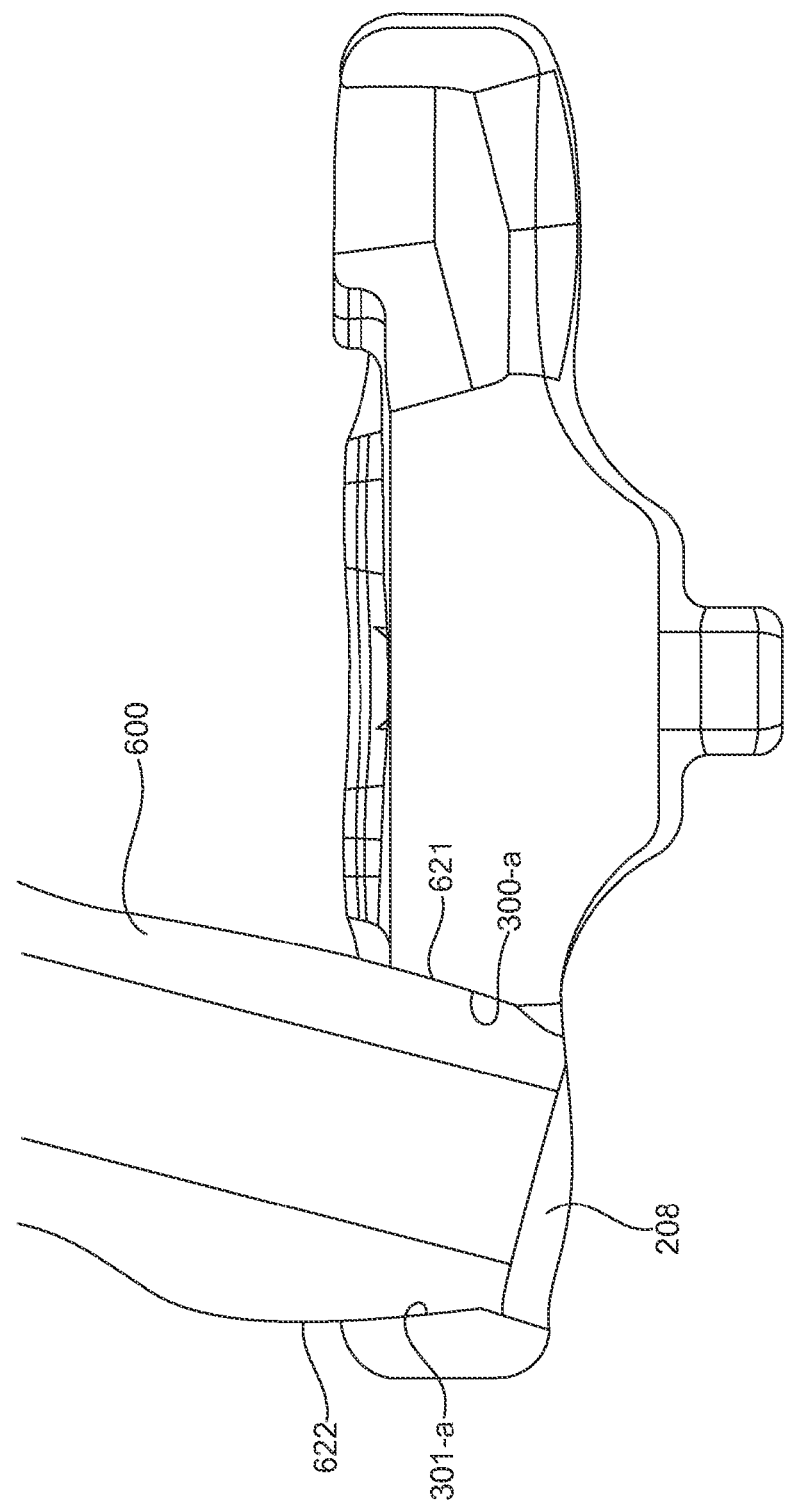
FIG. 14 is a cross sectional view of a fusion plate and fastener instrument consistent with the technology of the present application.

Another instrument suitable for use with the fusion plate described herein is shown in FIGS. 13 and 14. The instrument 600 includes a shaft portion 610 and a fastener engagement end 620. Rather than having a spherical shape, the fastener engagement end 620 of instrument 620 has a geometry that mates perfectly with the fastener bore 208. As shown in FIG. 13, this includes a vertical wall 621 for mating with the vertical portion 301-a and an angled wall 622 for mating with the angled portion 300-a. The instrument 600 may also include a distal vertical end 623 where the angled wall 622 straightens out to form a vertical segment at the very distal end of the instrument 600.

With reference to FIG. 14, a feature of the instrument 600 is that rotating the instrument 600 180 degrees and positioning it in the fastener bore 208 aligns the instrument 600 at the most extreme angle permitted by the fastener bore 208. As shown in FIG. 14, when positioned in this rotated configuration, the angled wall 622 rests against the vertical portion 301-a and the straight wall 621 rests against the angled portion 300-a.

Finally, a cover plate that corresponds to the fusion plate is selected and coupled to the fusion plate. For example, the connecting pin may be threaded through the cover plate bore and fusion plate bore into the internal threads of the threaded connector to couple the cover plate, fusion plate, and spacer.

The implant may be supplemented with bone growth promoting substances to facilitate fusion of adjacent vertebrae between spinous processes, laminae, transverse processes, facets, and/or other spinal structures. The bone growth promoting substances may be spaced from the implant, placed adjacent the implant, sandwiched between the implant and underlying bone, placed inside the implant, coated onto the implant, and/or otherwise placed relative to the implant. If it is coated onto the implant, it may cover the entire implant or only selected portions of the implant such as the extensions, fasteners, spinous process contacting portions of the spacer, and/or other portions.

In some embodiments, bone growth promoting materials are placed within the spacer before or after the spacer is implanted but before the fusion plate is coupled to the spacer. When bone growth promoting materials are placed within the spacer after it has been implanted but before the fusion plate has been coupled to the spacer, the surgeon has improved access to place the materials in the spacer as well as improved visibility.

As used herein, bone growth promoting substances may include bone paste, bone chips, bone strips, structural bone grafts, platelet derived growth factors, bone marrow aspirate, stem cells, bone growth proteins, bone growth peptides, bone attachment proteins, bone attachment peptides, hydroxylapatite, calcium phosphate, other suitable bone growth promoting substances, and/or combinations thereof.

The implant and any associated cerclage or other components may be made of any suitable biocompatible material including among others metals, resorbable ceramics, non-resorbable ceramics, resorbable polymers, and non-resorbable polymers. Some specific examples include stainless steel, titanium and its alloys including nickel-titanium alloys, tantalum, hydroxylapatite, calcium phosphate, bone, zirconia, alumina, carbon, bioglass, polyesters, polylactic acid, polyglycolic acid, polyolefins, polyamides, polyimides, polyacrylates, polyketones, fluoropolymers, and/or other suitable biocompatible materials and combinations thereof.

Various methods, systems and devices for treating spinal fractures are disclosed. While detailed descriptions of one or more embodiments have been provided above, various alternatives, modifications, and equivalents are possible. Therefore, the above description should not be taken as limiting the scope of possible embodiments, which is defined by the appended claims.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:
1. A fusion plate comprising:
a main body portion having a forward face and a rearward face opposed to the forward face;
a first extension side portion having a forward face and a rearward face opposed to the forward face and extending away from a first side of the main body; and
a first bore in the first extension side portion extending from the rearward face to the forward face, the first bore comprising:
a first opening in the rearward face having a first diameter extending from a first side of the first opening closest to the main body to an opposing side of the first opening;
a second opening in the forward face having a second diameter extending from a first side of the second opening closest to the main body to an opposing side of the first opening; and
a throat portion located intermediate the first opening and the second opening and having a third diameter extending from a first side of the throat portion closest to the main body to an opposing side of the throat portion;
wherein the third diameter is shorter than the first diameter and the second diameter; and
wherein the first bore includes a first side wall portion proximate the main body and a second side wall portion opposite the first side wall portion;
the first side wall portion includes an angled portion extending from the first opening to a first point intermediate the first opening and the second opening and a vertical wall portion extending from the first point to the second opening; and
the second side wall portion includes a vertical portion extending from the first opening to a second point intermediate the first opening and the second opening and an angled portion extending from the second point to the second opening.

2. The fusion plate of claim 1, wherein the first diameter of the first opening has a first end proximate the main body and a second end opposite the first end and the second diameter of the second opening has a first end proximate the main body and a second end opposite the first end, and wherein the first end of the first diameter of the first opening is positioned closer to the main body than the first end of the second diameter and wherein the second end of the first diameter is positioned closer to the main body than the second end of the second diameter.

3. The fusion plate of claim 1, wherein the first side wall angled portion is oriented parallel with the second side wall angled portion.

4. The fusion plate of claim 1, wherein the second point is closer to the rearward face than the first point.

5. The fusion plate of claim 1, wherein the first extension side portion includes a second bore identical to the first bore.

6. The fusion plate of claim 5, wherein the second bore is located lateral to the first bore.

7. The fusion plate of claim 1, further comprising:
a second extension side portion extending away from a second side of the main body that is opposite the first side of the main body.

8. The fusion plate of claim 7, wherein the second extension side portion includes a first bore identical to the first bore in the first extension side portion.

9. The fusion plate of claim 1, wherein the first bore limits movement of a screw inserted therethrough in a direction perpendicular to a longitudinal axis of the fusion plate.

10. The fusion plate of claim 1, further comprising a recess formed in the rearward face of the main body and the first extension side portion and adapted for receiving a cover plate.

11. An implant configured to be interposed between opposing faces of two bones to be fused together, the implant comprising:
a spacer configured to fit between the opposing sides of the two bones to promote fusion of the two bones, the spacer having a forward portion, a rearward portion, a top portion, a bottom portion, and two side portions, the rearward portion comprising at least one cavity;
a fusion plate coupled to the spacer comprising:
a main body portion having a forward face and a rearward face opposed to the forward face;
a first extension side portion having a forward face and a rearward face opposed to the forward face and extending away from a first side of the main body; and
a first bore in the first extension side portion extending from the rearward face to the forward face, the first bore comprising:
a first opening in the rearward face having a first diameter extending from a first side of the first opening closest to the main body to an opposing side of the first opening;
a second opening in the forward face having a second diameter extending from a first side of the second opening closest to the main body to an opposing side of the first opening; and
a throat portion located intermediate the first opening and the second opening and having a third diameter extending from a first side of the throat portion closest to the main body to an opposing side of the throat portion;
wherein the third diameter is shorter than the first diameter and the second diameter; and
wherein the first bore includes a first side wall portion proximate the main body and a second side wall portion opposite the first side wall portion;
the first side wall portion includes an angled portion extending from the first opening to a first point intermediate the first opening and the second opening and a vertical wall portion extending from the first point to the second opening; and
the second side wall portion includes a vertical portion extending from the first opening to a second point intermediate the first opening and the second opening and an angled portion extending from the second point to the second opening; and
a plurality of fasteners comprising at least a first fastener extending through the first bore and exiting out of the second opening and configured to couple the implant to an endplate of a first bone.

12. The implant of claim 11, wherein the first diameter of the first opening has a first end proximate the main body and a second end opposite the first end and the second diameter of the second opening has a first end proximate the main body and a second end opposite the first end, and wherein the first end of the first diameter of the first opening is positioned closer to the main body than the first end of the second diameter and wherein the second end of the first diameter is positioned closer to the main body than the second end of the second diameter.

13. The implant of claim 11, wherein at least a portion of the fusion plate is received within the at least one cavity.

14. The implant of claim 11, wherein the first extension side portion is configured to extend beyond at least one of the top portion or the bottom portion of the spacer.

15. The implant of claim 11, wherein the spacer further comprises a spacer bore extending from the forward portion to the rearward portion and wherein the main body portion of the fusion plate further comprises a fusion plate bore extending from the forward face to the rearward face and the fusion plate is coupled to the spacer with a fastener that extends through the fusion plate bore and the spacer bore.

16. The implant of claim 15, wherein the fusion plate bore and the spacer bore are coaxially aligned when the fusion plate is disposed in the cavity.

17. The implant of claim 11, wherein the first bore limits movement of the at least one fastener extending therethrough in a direction perpendicular to a longitudinal axis of the fusion plate.

18. The implant of claim 11, further comprising a recess formed in the rearward face of the main body and the first extension side portion and adapted for receiving a cover plate.

19. A method of implanting an implant comprising:
selecting a spacer and implanting the spacer between two bone segments;
coupling a fusion plate to a rearward face of the implanted spacer, wherein the fusion plate comprises:
a first extension side portion having a forward face and a rearward face opposed to the forward face and extending away from a first side of the main body; and
a first bore in the first extension side portion extending from the rearward face to the forward face, the first bore comprising:
a first opening in the rearward face having a first diameter extending from a first side of the first opening closest to the main body to an opposing side of the first opening;
a second opening in the forward face having a second diameter extending from a first side of the second opening closest to the main body to an opposing side of the first opening; and
a throat portion located intermediate the first opening and the second opening and having a third diameter extending from a first side of the throat portion closest to the main body to an opposing side of the throat portion;
wherein the third diameter is shorter than the first diameter and the second diameter; and
wherein the first bore includes a first side wall portion proximate the main body and a second side wall portion opposite the first side wall portion;
the first side wall portion includes an angled portion extending from the first opening to a first point intermediate the first opening and the second opening and a vertical wall portion extending from the first point to the second opening; and
the second side wall portion includes a vertical portion extending from the first opening to a second point intermediate the first opening and the second opening and an angled portion extending from the second point to the second opening;
inserting a fastener through the first bore and positioning the fastener at an angle permitted by the first bore; and
driving the fastener into a bone segment.

20. The method of claim 19, further comprising coupling a cover plate to the fusion plate, wherein the cover plate is configured to prevent the fastener from backing out of the first bore.

21. The method of claim 19, wherein inserting the fastener through the first bore and positioning the fastener at an angle permitted by the first bore is carried out using an instrument having a distal end shaped and configured to position the fastener at the largest angle permitted by the first bore.

\* \* \* \* \*